(12) United States Patent
Chen

(10) Patent No.: US 11,191,900 B2
(45) Date of Patent: Dec. 7, 2021

(54) INTRAVENOUS INFUSION SYSTEM WITH REAL-TIME INFUSION RATE MONITORING AND CLOSED-LOOP INFUSION RATE CONTROL

(71) Applicant: Jingkuang Chen, Rochester, NY (US)

(72) Inventor: Jingkuang Chen, Rochester, NY (US)

( * ) Notice: Subject to any disclaimer, the term of this patent is extended or adjusted under 35 U.S.C. 154(b) by 65 days.

(21) Appl. No.: 16/861,355

(22) Filed: Apr. 29, 2020

(65) Prior Publication Data

US 2020/0345934 A1 Nov. 5, 2020

Related U.S. Application Data

(60) Provisional application No. 62/841,773, filed on May 1, 2019.

(51) Int. Cl.
*A61M 5/172* (2006.01)
*A61M 5/142* (2006.01)

(52) U.S. Cl.
CPC .......... *A61M 5/1723* (2013.01); *A61M 5/142* (2013.01); *A61M 2005/14208* (2013.01); *A61M 2005/1726* (2013.01); *A61M 2205/3331* (2013.01); *A61M 2205/3553* (2013.01); *A61M 2205/3592* (2013.01); *A61M 2205/50* (2013.01)

(58) Field of Classification Search
CPC .......... A61M 2005/14208; A61M 2005/1726; A61M 2205/3331; A61M 2205/3553; A61M 2205/3592; A61M 2205/50; A61M 5/142; A61M 5/1723; A61M 5/14; A61M 5/00; A61M 5/168; A61M 5/172; A61M 2205/33; A61M 2205/35; A61M 2205/3546; A61M 2205/3576

See application file for complete search history.

(56) References Cited

U.S. PATENT DOCUMENTS

2019/0275247 A1* 9/2019 Eibl ...................... A61B 8/4236
2020/0237977 A1* 7/2020 Panotopoulos ..... A61M 1/0058

* cited by examiner

*Primary Examiner* — Jason E Flick
(74) *Attorney, Agent, or Firm* — Demian K. Jackson; Jackson IPG PLLC

(57) ABSTRACT

An intravenous infusion system with real-time infusion rate monitoring and closed-loop infusion rate control is disclosed. The intravenous infusion system comprises: an infusion module, providing drug solution through an intravenous catheter; a flow sensor module, installed around an outer periphery of the intravenous catheter, transmitting ultrasounds to the intravenous catheter and receiving ultrasounds reflected or penetrated therefrom to determine a real-time volumetric flow rate of the drug solution in the intravenous catheter, and converting the real-time volumetric flow rate into a flow rate electronic signal; and a communicating module, electrically and signally connected with the flow sensor module, receiving the flow rate electronic signal and delivering the flow rate electronic signal to an external agent connected thereto.

19 Claims, 11 Drawing Sheets

INTRAVENOUS INFUSION SYSTEM WITH REAL-TIME INFUSION RATE MONITORING AND CLOSED-LOOP INFUSION RATE CONTROL

CROSS-REFERENCE TO RELATED APPLICATIONS

This application claims priority under 35 U.S.C. section 119(e) to U.S. provisional application Ser. No. 62/841,773 titled "Intravenous Infusion System with Real-Time Infusion Rate Monitoring and Closed-Loop Infusion Rate Control," filed on May 1, 2019, which is incorporated herein in its entirety for all purposes.

FIELD OF THE INVENTION

The present invention relates to an intravenous infusion system. More particularly, the present invention relates to an intravenous infusion system with real-time infusion rate monitoring and closed-loop infusion rate control.

BACKGROUND OF THE INVENTION

An intravenous infusion uses a controlled administration method to deliver medication into the bloodstream of a patient. The two main methods of intravenous infusion use either gravity or a pump to send medication into an intravenous catheter. A pump infusion system uses an infusion pump to input drug solution through an intravenous tubing with a consistent and predictable flow rate. Compared to a gravity drip intravenous system, which uses gravitational force to deliver drugs into the intravenous line, pumps are typically used when the medication dosage and infusion rate require more precise control.

One of the limits associated with the current intravenous setup is the lack of real-time infusing rate monitoring capability. A gravity drip intravenous system uses a roller clamp to adjust the infusion rate. Although the roller clamp can increase or decrease the infusion rate, the exact infusion rate cannot be ascertained on gravity drip intravenous systems. For an infusion system driven by a pump, the infusion rate is determined by the settings keyed in to the infusion pump. In order to guarantee the accuracy of the infusion rate setting, an infusion pump requires regular calibration. Additionally, due to the high accuracy needed for infusion rate control, high-precision mechanical parts and assemblies are needed for an infusion pump, resulting in high pump costs.

Nowadays many infusion systems work as stand-alone devices. Medical personnel have to check on the infusion process periodically to ensure the infusion process is working as expected. Constant monitoring is required for both gravity drip and pump infusion systems, and presents a significant workload for medical personnel, reducing the number of patients they can manage. A procedure solely managed by medical personnel also presents a potential risk of human error which may harm patient safety. Therefore, a solution to settle the aforementioned problem is desired.

SUMMARY OF THE INVENTION

This paragraph extracts and compiles some features of the present invention; other features will be disclosed in the follow-up paragraphs. It is intended to cover various modifications and similar arrangements included within the spirit and scope of the appended claims.

According to an aspect of the present invention, an intravenous infusion system with real-time infusion rate monitoring and closed-loop infusion rate control is disclosed. The intravenous infusion system comprises: an infusion module, providing drug solution through an intravenous catheter; a flow sensor module, installed around an outer periphery of the intravenous catheter, transmitting ultrasounds to the intravenous catheter and receiving ultrasounds reflected or penetrated therefrom to determine a real-time volumetric flow rate of the drug solution in the intravenous catheter, and converting the real-time volumetric flow rate into a flow rate electronic signal; and a communicating module, electrically and signally connected with the flow sensor module, receiving the flow rate electronic signal and delivering the flow rate electronic signal to an external agent connected thereto.

Preferably, the infusion module may be an infusion pump, or a set of a drip bag and a roller clamp.

The flow sensor module may comprise at least one flow sensor attached to the outer periphery of or connected in series with the intravenous catheter when an internal diameter of the intravenous catheter is substantially fixed. The flow sensor may be a hot-wire flow sensor, a differential-pressure-pair flow sensor, an electromagnetic flow sensor, or an ultrasonic flow sensor.

The communicating module may comprise: a processor, electrically and signally connected with the flow sensor module to receive the flow rate electronic signal; and a communicating element, electrically connected to and controlled by the processor to wiredly or wirelessly deliver the flow rate electronic signal to the external agent connected thereto for analysis and display. The communicating element may be a USB module, a Bluetooth module, or a Wi-Fi module.

According to the present invention, the flow sensor module may comprise: at least one ultrasound transducer, transmitting ultrasounds with a center frequency equal to or higher than 100 k Hz, receiving reflected ultrasounds from the intravenous catheter and transforming the reflected ultrasounds into a sensing electronic signal; and a processing unit, electrically connected to the at least one ultrasound transducer, comparing one transmitted ultrasound with a corresponding reflected ultrasound using the sensing electronic signal to find Doppler ultrasound frequency shift generated therefrom, calculating a linear flow rate of the drug solution with the Doppler ultrasound frequency shift, finding a flight time echo delay between two reflected ultrasounds generated from the same transmitted ultrasound from two opposite inner surfaces of the intravenous catheter, respectively, to calculate the internal diameter of the intravenous catheter, determining the real-time volumetric flow rate of the drug solution in the intravenous catheter by multiplying the linear flow rate and a cross-sectional area calculated from the internal diameter of the intravenous catheter, and converting the real-time volumetric flow rate into the flow rate electronic signal. The ultrasound transducer may be a piezoelectric transducer, a capacitive micromachined ultrasound transducer, or a piezoelectric micromachined ultrasound transducer.

The flow sensor module may also comprise: at least one pair of face-to-face detecting elements fitted around the intravenous catheter, wherein the face-to-face detecting element comprises at least one ultrasound transducer, transmitting ultrasounds with a center frequency equal to or higher than 100 k Hz, receiving reflected or penetrated ultrasounds from the intravenous catheter and transforming the reflected or penetrated ultrasounds into a sensing electronic signal;

and a processing unit, electrically connected to the at least one pair of face-to-face detecting elements, comparing one transmitted ultrasound with a corresponding penetrated ultrasound using the sensing electronic signal to find Doppler ultrasound frequency shift generated therefrom, calculating a linear flow rate of the drug solution with the Doppler ultrasound frequency shift, finding a flight time echo delay between two reflected ultrasounds generated from the same transmitted ultrasound from two opposite inner surfaces of the intravenous catheter, respectively, to calculate the internal diameter of the intravenous catheter, determining the real-time volumetric flow rate of the drug solution in the intravenous catheter by multiplying the linear flow rate and a cross-sectional area calculated from the internal diameter(s) of the intravenous catheter, and converting the real-time volumetric flow rate into the flow rate electronic signal. The ultrasound transducer may be a piezoelectric transducer, a capacitive micromachined ultrasound transducer, or a piezoelectric micromachined ultrasound transducer.

Preferably, the external agent is a micro-controller and electrically connected to a control unit of the infusion pump, comparing the real-time volumetric flow rate to a pump target rate of the infusion pump in a clinical setting and adjusts a pump repetition rate of the infusion pump via the control unit such that the flow rate of the drug solution from the infusion pump approaches the pump target rate. The external agent may be a smart phone, a tablet or a computer.

According to the present invention, an application (APP) may be installed in the smart phone, a tablet or a computer. The APP is initiated to calculate and record the total volume of drug solution infused from the onset of the process by integrating the real-time volumetric flow rate over the time elapsed, compare the real-time volumetric flow rate and the total volume of drug to an infusion rate and a dosage setting, respectively, and actuate an alert message from the external agent when the total volume of drug is close to the dosage setting. The APP can be initiated to actuate an alert in sound, vibration, light signal, or visual images on a screen of the external agent when the real-time volumetric flow rate falls out of a safety window when the infusion module is a set of a drip bag and a roller clamp. The APP can also be integrated with an infusion drug database such that all settings of the external agent, an instantaneous infusion rate, and a real-time dosage are regularly checked with the infusion drug database to ensure safety of the patient during an infusion process.

When the infusion module is a set of a drip bag and a roller clamp, if a slow-down of the real-time volumetric flow rate is obtained and lower than a preset value, the APP actuates the external agent to send an alert signal in sound, vibration, light signal, and/or images visual images on a screen of the external agent to alert the medical personnel to take action to end an infusion process at the end of the infusion process. When the infusion module is an infusion pump, the intravenous infusion system forms a closed-loop control on infusion with a micro-controller and electrically connected to a control unit of the infusion pump corrects infusion rate deviation from a clinical setting and/or stops the infusion process according to the clinical setting. If the real-time volumetric flow rate is higher than the clinical setting, the pump repetition rate of the infusion pump will be lowered by the micro-controller; if the real-time volumetric flow rate is lower than the clinical setting, the pump repetition rate of the infusion pump will be increased by the micro-controller.

This invention discloses a smart intravenous infusion system which makes use of the flow sensor module for real-time infusion rate measurement and infusion process management. The measured real-time volumetric flow rate is then used for infusion rate control, either manually through a roller clamp by medical personnel for a gravity drip intravenous system, or electronically for an infusion pump.

DETAILED DESCRIPTION OF THE PREFERRED EMBODIMENTS

The present invention will now be described more specifically with reference to the following embodiments.

Figure 1:
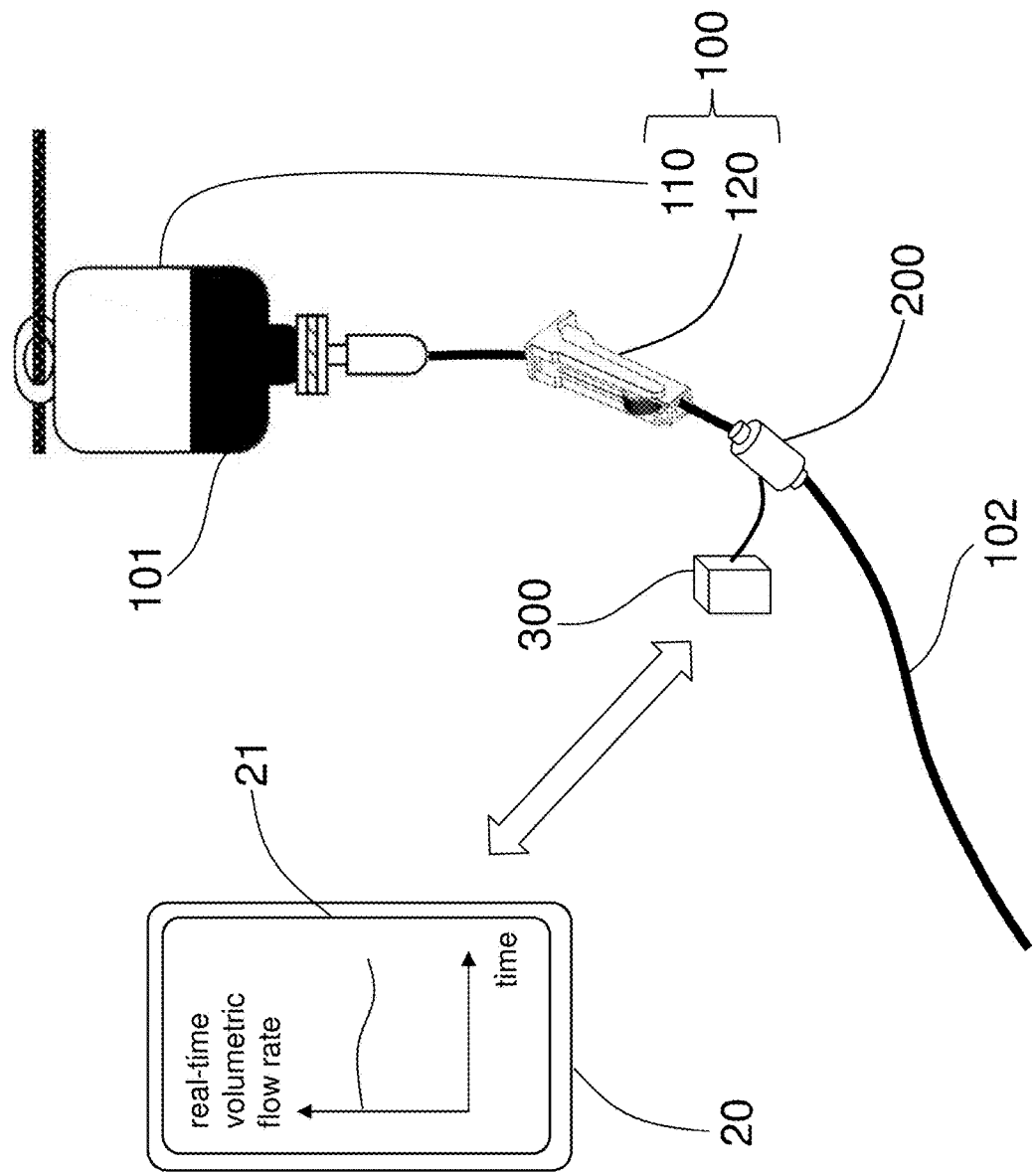
FIG. 1 shows an embodiment of an intravenous infusion system with real-time infusion rate monitoring according to the present invention.

Please refer to FIG. 1. An embodiment of an intravenous infusion system 10 with real-time infusion rate monitoring according to the present invention is disclosed. The intravenous infusion system 10 comprises an infusion module 100, a flow sensor module 200 and a communicating module 300. The infusion module 100 can provide drug solution 101 through an intravenous catheter 102. In this embodiment, the infusion module 100 is a set of a drip bag 110 and a roller clamp 120. There is a syringe needle (not shown) connected in the end of the intravenous catheter 102 to infuse drug solution 101 into human body.

The flow sensor module 200 is installed around an outer periphery of the intravenous catheter 102. In general, the flow sensor module 200 can transmit ultrasounds to the intravenous catheter 102. It can receive ultrasounds reflected or penetrated from the intravenous catheter 102 to determine a real-time volumetric flow rate of drug solution 101 in the intravenous catheter 102 as well. The real-time volumetric flow rate is converted into a flow rate electronic signal by the flow sensor module 200. There are many implements of the flow sensor module 200. If an internal diameter of the intravenous catheter 102 is substantially fixed and made to within a high degree of accuracy, the flow sensor module 200 may comprise at least one flow sensor attached to the outer periphery of the intravenous catheter 102. Preferably, the flow sensor can be a hot-wire flow sensor, a differential-pressure-pair flow sensor, an electromagnetic flow sensor, or an ultrasonic flow sensor.

Figure 2:
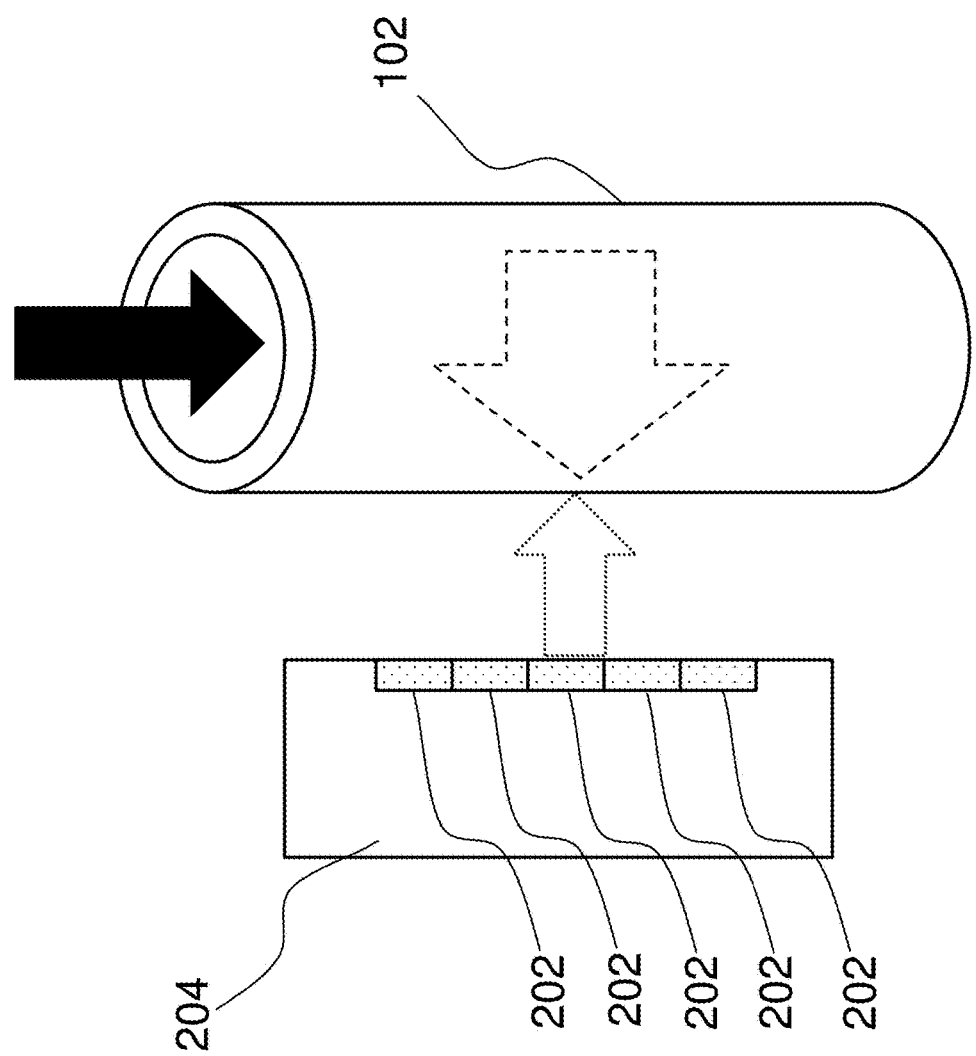
FIG. 2 shows an example of a flow sensor module.
Figure 3:
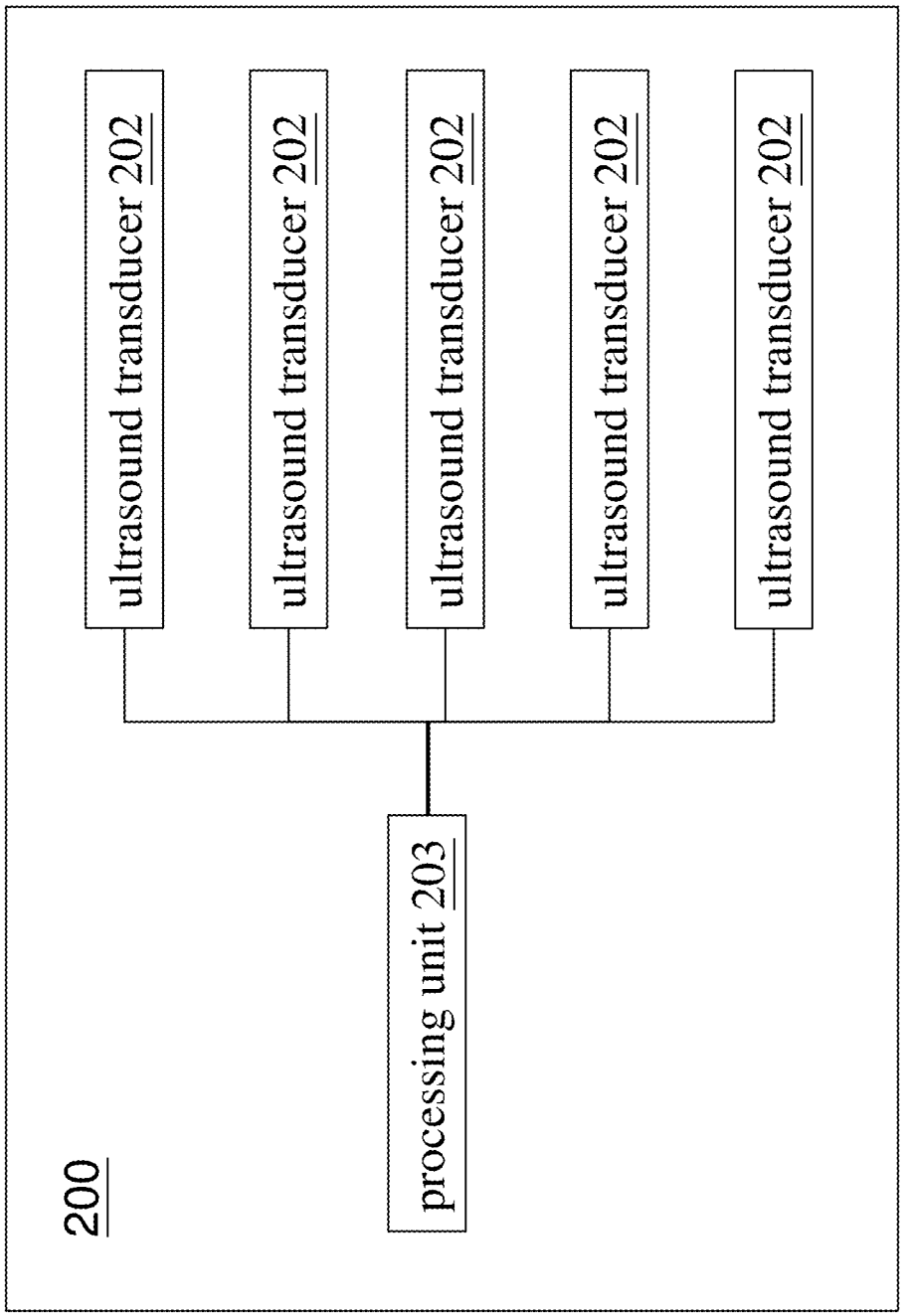
FIG. 3 is a block diagram of the flow sensor module.

Please see FIG. 2 and FIG. 3. FIG. 2 shows another example of the flow sensor module 200. FIG. 3 is a block diagram of the flow sensor module 200. The flow sensor module 200 comprises several ultrasound transducers 202 and a processing unit 203. The ultrasound transducers 202 and the processing unit 203 are installed in a substrate 204. Working portions of the ultrasound transducers 202 face externally so that the ultrasounds can be transmitted to the intravenous catheter 102 and reflected ultrasounds can also be received. According to the present invention, the number of the ultrasound transducers 202 is at least one. If only one ultrasound transducer 202 is used, only one data can be obtained at one time. If many ultrasound transducers 202 are used, more data can be obtained at one time. Redundant data can be used for other analysis or increasing accuracy of measurement. In this embodiment, there are 5 ultrasound transducers 202 arranged in a line, from top to bottom. In other embodiments, the number of the ultrasound transducers 202 is not limited to 4 as shown in FIG. 2 and FIG. 3. It can be 2, 3, 5 or more.

The ultrasound transducer 202 generates and transmits ultrasounds as shown by a dot-framed arrow. In order to have good functioning results, the ultrasounds from the ultrasound transducer 202 should be with a center frequency equal to or higher than 100 k Hz, e.g. 1.0M Hz. The arrangement of the ultrasound transducers 202 may not limit to a linear arrangement; they can be arranged two-dimensionally on a plane or on a curved surface. Each of the ultrasound transducer 202 can receive reflected ultrasounds (shown by a dash-framed arrow) from the intravenous catheter 102. Meanwhile, the ultrasound transducer 202 transforms the reflected ultrasounds into a sensing electronic signal for further applications. Preferably, the ultrasound transducer 202 may be a piezoelectric transducer, a capacitive micromachined ultrasound transducer, or a piezoelectric micromachined ultrasound transducer.

Figure 4:
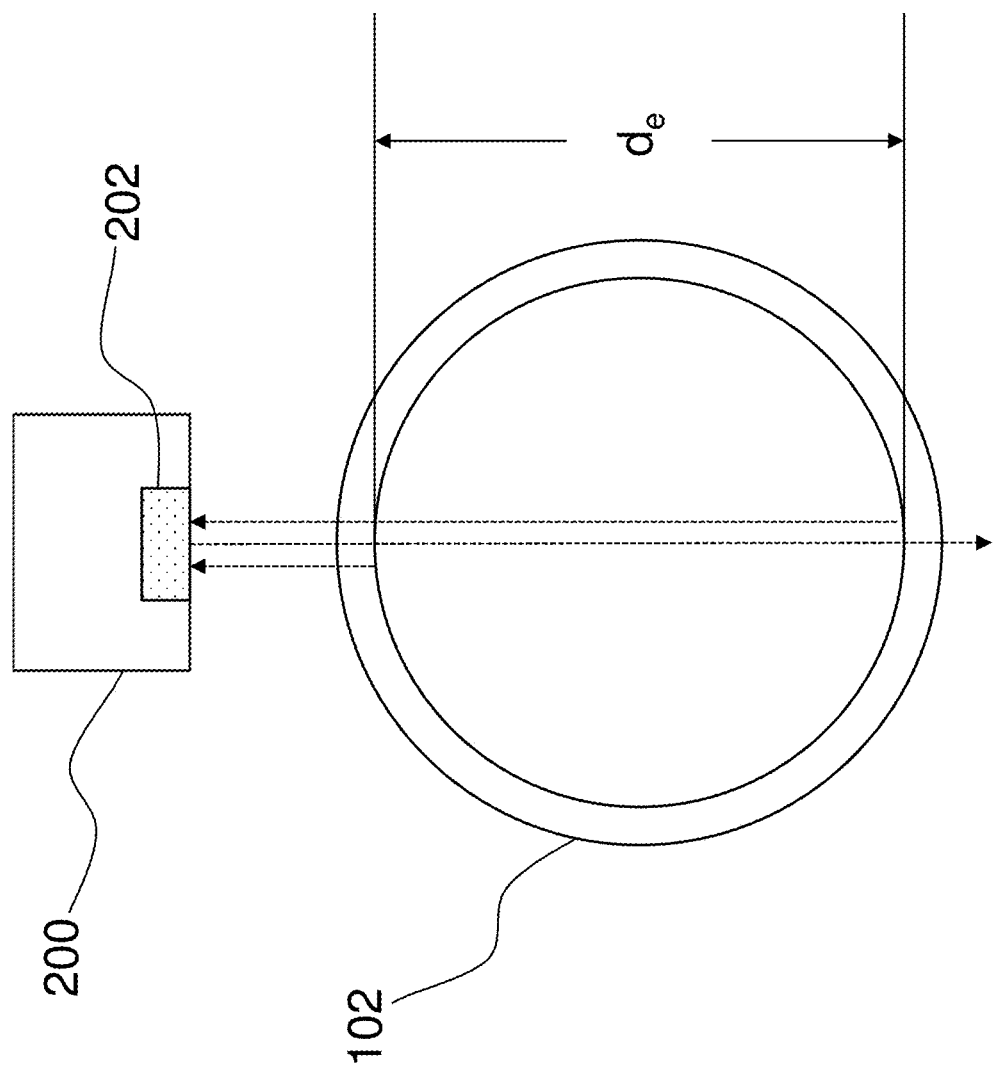
FIG. 4 illustrates one ultrasound transducer receives different kind of reflected ultrasound from the same transmitted ultrasound from the ultrasound transmitter.

The processing unit 203 is electrically connected to the ultrasound transducers 202. The processing unit 203 may be an integrated circuit chip or a multi-chip module with necessary auxiliary components. The processing unit 203 compares one transmitted ultrasound with a corresponding reflected ultrasound using the sensing electronic signal to find Doppler ultrasound frequency shift generated from the reflected ultrasound. The drug solution 101 flows as the direction of a solid arrow shows. As the drug solution 101 flows, any reflected ultrasound from the drug solution 101 will cause a change in frequency comparing with the transmitted ultrasound which the reflected ultrasound comes from. It is called Doppler ultrasound frequency shift and is used widely for fluid velocity detection. Therefore, the processing unit 203 can calculate a linear flow rate of the drug solution 101 with the Doppler ultrasound frequency shift. In addition to the linear flow rate, the processing unit 203 can find a flight time echo delay between two reflected ultrasounds generated from the same transmitted ultrasound from two opposite inner surfaces of the intravenous catheter 102, respectively, to calculate the internal diameter of the intravenous catheter 102. To have a better understanding of how the internal diameter of the intravenous catheter 102 is calculated, please refer to FIG. 4. It illustrates one ultrasound transducer 202 that receives different kind of reflected ultrasound from the same transmitted ultrasound from itself. After the transmitted ultrasound is generated from the ultrasound transducer 202, it may propagate toward the intravenous catheter 102, penetrating two opposite inner surfaces of the intravenous catheter 102, as the dashed arrow with head down shown. The transmitted ultrasound may also be reflected by the two opposite inner surfaces, as the dashed arrows with head up shown. The flight time echo delay can be found in the two reflected ultrasounds. With the flight time echo delay, many existing methods can be applied to calculate the internal diameter $d_e$ of the intravenous catheter 102. Once the internal diameter $d_e$ of the intravenous catheter 102 is obtained, a cross-sectional area of the intravenous catheter 102 can be available. For example, the cross-sectional area of the intravenous catheter 102 may be mathematically derived by $\pi(d_e)^2/4$. The flow sensor module 200 illustrated in FIG. 2 is suitable for the intravenous catheter 102 which may differ in internal diameter from catheter to catheter due to catheter material properties or manufacture process. It is natural if soft materials are chosen for the intravenous catheter 102, like many of the on-market infusion catheters. Meanwhile, the processing unit 203 can determine the real-time volumetric flow rate of the drug solution 101 in the intravenous catheter 102 by multiplying the linear flow rate and the cross-sectional area calculated from the internal diameter $d_e$ of the intravenous catheter 102. Of course, the processing unit 203 is in charge of converting the real-time volumetric flow rate into the flow rate electronic signal. As the air-fluid interface forms a sharp acoustic impedance boundary for ultrasound, the array of ultrasound transducers 202 also identifies the presence of bubbles in the intravenous catheter 102. The flow sensor module 200 illustrated by FIG. 2 to FIG. 4 is suitable for the drug solution with scattering particles. The scattering particles are notable particles, such as large drug particles, large biosimilar molecules, etc., in the drug solution. The scattering particles help reflecting ultrasounds with Doppler ultrasound frequency shift.

Figure 5:
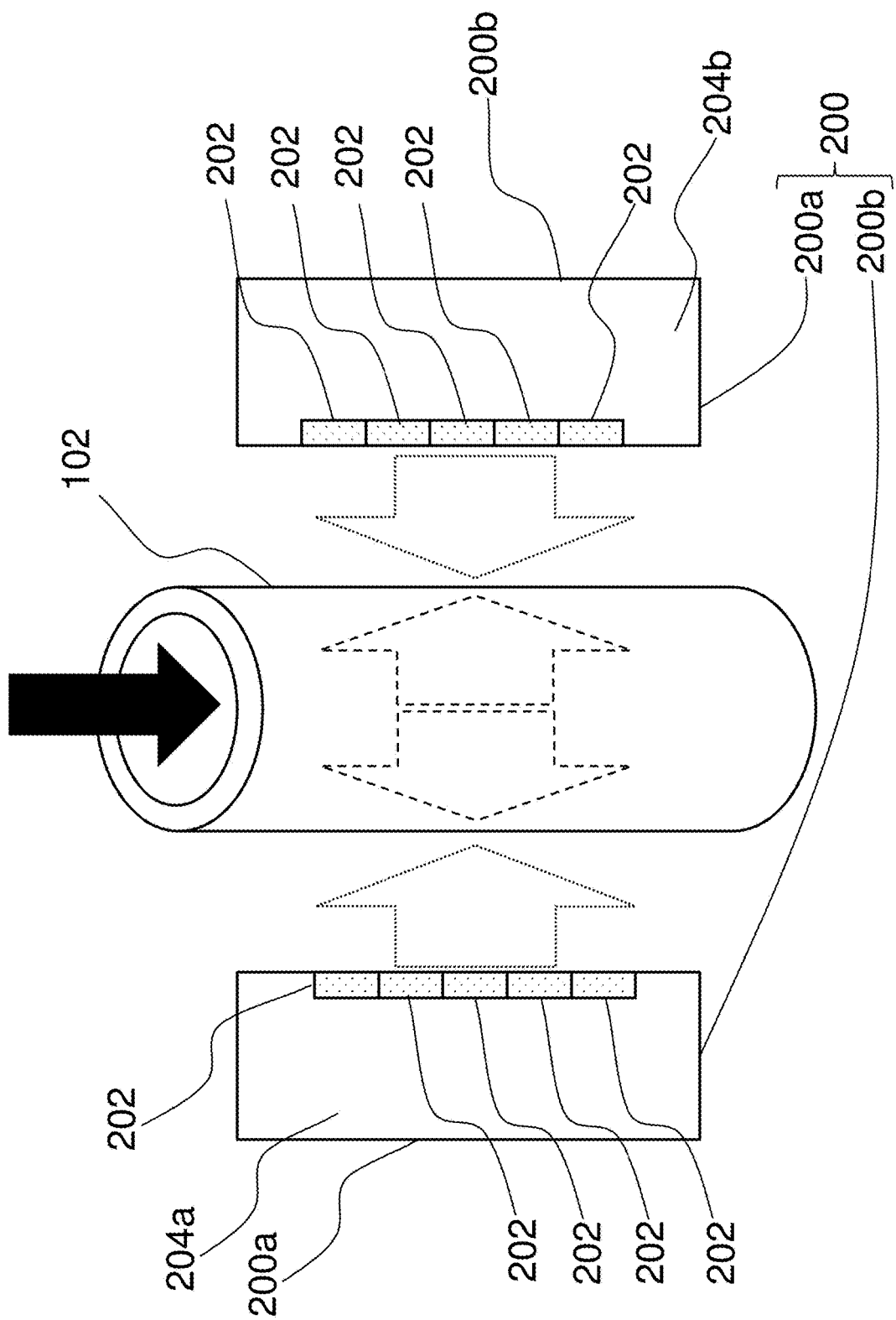
FIG. 5 shows another example of the flow sensor module with face-to-face detecting elements.

In another example, the flow sensor module 200 may have different type. Please see FIG. 5. It shows another example of the flow sensor module 200 with face-to-face detecting elements. The flow sensor module 200 comprises one pair of face-to-face detecting elements (a first face-to-face detecting element 200a and a second face-to-face detecting element 200b) and a processing unit 213. According to the spirit of the present invention, the number of pair of face-to-face detecting elements is not limited to 1. It is at least one and FIG. 5 shows one of the designs. The first face-to-face detecting element 200a and the second face-to-face detecting element 200b are fitted around the intravenous catheter 102. Each of the face-to-face detecting element may just contact the intravenous catheter 102 with its ultrasound transducers or keep a tiny space therebetween. Components of the first face-to-face detecting element 200a and of the second face-to-face detecting element 200b are the same. They both include an array of 5 ultrasound transducers 202. Functions of the ultrasound transducer 202 are the same as that in the previous example, except the ultrasound transducer 202 can further receive penetrated ultrasounds from the intravenous catheter 102 and transform both the reflected or penetrated ultrasounds into the sensing electronic signal. Of course, the number of ultrasound transducer 202 is not limited to 5 and can be at least one. Similarly, the ultrasound transducers 202 may be a piezoelectric transducer, a capacitive micromachined ultrasound transducer, or a piezoelectric micromachined ultrasound transducer.

The ultrasound transducers 202 of the first face-to-face detecting element 200a are installed in a substrate 204a. Working portions of the ultrasound transducers 202 face externally. In this example, 5 ultrasound transducers 202 of the first face-to-face detecting element 200a are arranged in a line, from top to bottom. The ultrasound transducers 202 of the second face-to-face detecting element 200b are installed in a substrate 204b. Working portions of the ultrasound transducers 202 face externally, too. 5 ultrasound transducers 202 of the first face-to-face detecting element 200a are arranged in a line, from top to bottom. With this design, when the first face-to-face detecting element 200a and the second face-to-face detecting element 200b are mounted and fixed to the intravenous catheter 102, a transmitted ultrasound (shown by the dot-framed arrow heading right) from the ultrasound transducers 202 of the first face-to-face detecting element 200a can penetrate the intravenous catheter 102 and the penetrated ultrasound (shown by the dash-framed arrow heading right) can be received by the ultrasound transducers 202 of the first face-to-face detecting element 200a. On the contrary, a transmitted ultrasound (shown by the dot-framed arrow heading left) from the ultrasound transducers 202 of the second face-to-face detecting element 200b can penetrate the intravenous catheter 102 and the penetrated ultrasound (shown by the dash-framed arrow heading left) can be received by the ultrasound transducers 202 of the second face-to-face detecting element 200b.

Figure 6:
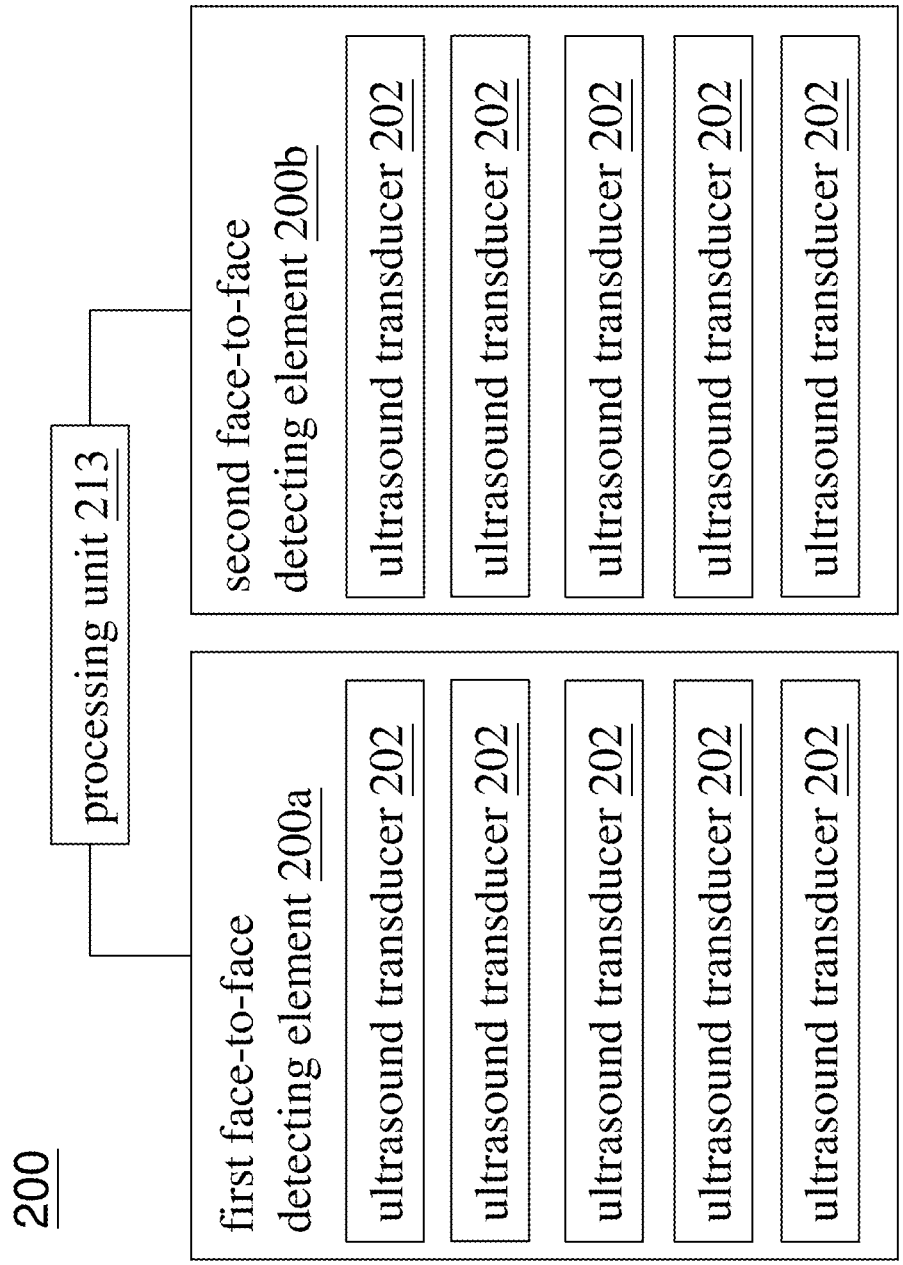
FIG. 6 is a block diagram of the flow sensor module with a pair of face-to-face detecting elements.
Figure 7:
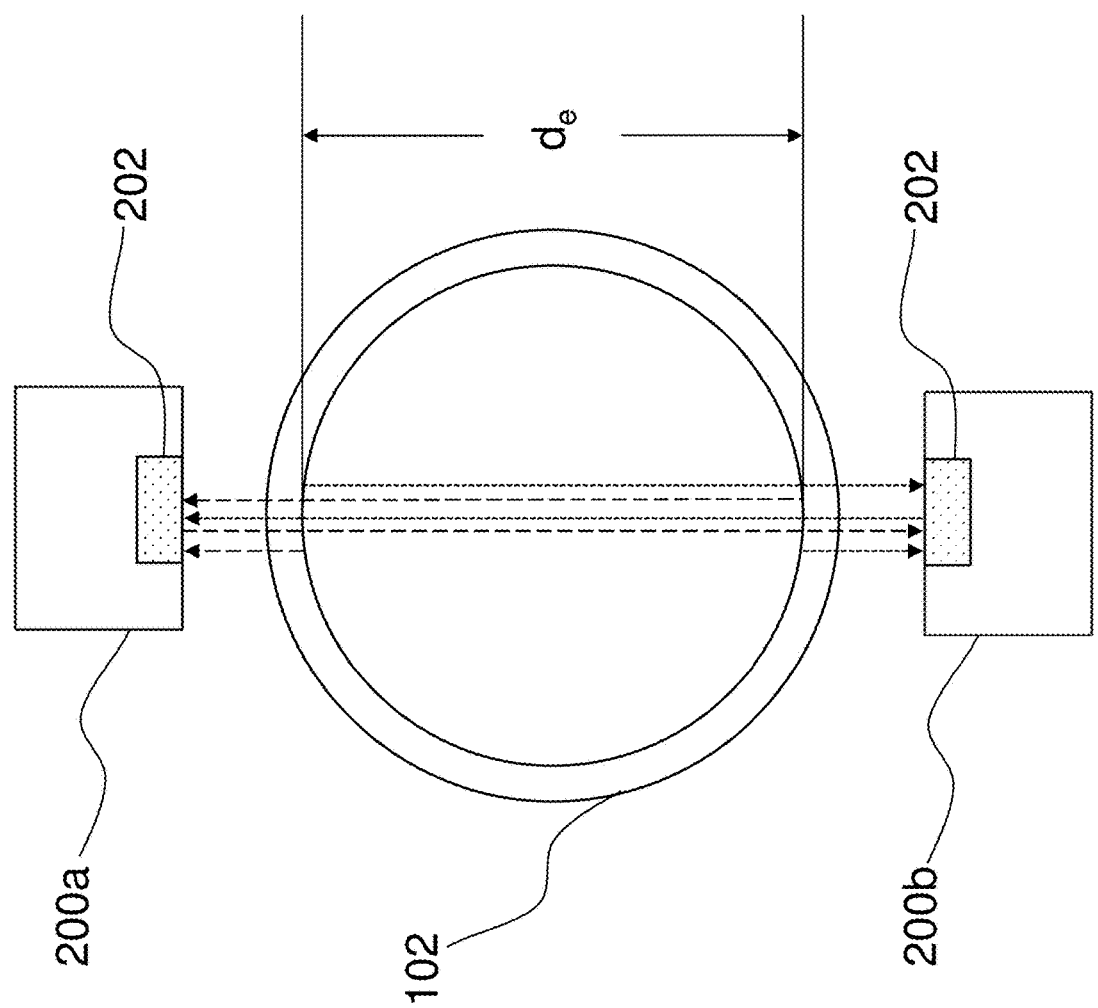
FIG. 7 illustrates ultrasound transducers receive different kind of reflected ultrasound from the same transmitted ultrasound from the ultrasound transmitter in the other face-to-face detecting element.

Please see FIG. 6. It is a block diagram of the flow sensor module 200 with a pair of face-to-face detecting elements. The processing unit 213 is electrically connected to the pair of face-to-face detecting elements. It should be noticed that the processing unit 213 can be designed to locate in either the substrate 204a or the substrate 204b. The processing unit 213 can connect the components in the other substrate by wiring. The processing unit 213 compare one transmitted ultrasound from the ultrasound transducer 202 (no matter which face-to-face detecting element it belongs to) with a corresponding penetrated ultrasound using the sensing electronic signal (from the ultrasound transducers 202 in the other face-to-face detecting element) to find Doppler ultrasound frequency shift generated from the penetrated ultrasound. Thus, the processing unit 213 can calculate a linear flow rate of the drug solution 101 with the Doppler ultrasound frequency shift. Similarly, the processing unit 213 can find a flight time echo delay between two reflected ultrasounds generated from the same transmitted ultrasound from two opposite inner surfaces of the intravenous catheter 102, respectively, to calculate the internal diameter of the intravenous catheter 102. Please refer FIG. 7. It illustrates ultrasound transducers 202 receive different kind of reflected ultrasound from the same transmitted ultrasound from the ultrasound transducers 202 in the other face-to-face detecting element.

After the transmitted ultrasound is generated from the ultrasound transducer 202 in the first face-to-face detecting element 200a, it propagates toward the intravenous catheter 102, penetrating two opposite inner surfaces of the intravenous catheter 102, as the dashed arrow with head down shown. The transmitted ultrasound may also be reflected by the two opposite inner surfaces, as the dashed arrows with head up shown. One flight time echo delay can be found in the two reflected ultrasounds by the ultrasound transducers 202 in the first face-to-face detecting element 200a. Similarly, after the transmitted ultrasound is generated from the ultrasound transducer 202 in the second face-to-face detecting element 200b, it propagates toward the intravenous catheter 102, penetrating two opposite inner surfaces of the intravenous catheter 102, as the dotted arrow with head up shown. The transmitted ultrasound may also be reflected by the two opposite inner surfaces, as the dashed arrows with head down shown. The other flight time echo delay can be found in the two reflected ultrasounds by the ultrasound transducers 202 in the second face-to-face detecting element 200b. There might be difference between the two flight time echo delays and it leads to different cross-sectional area. However, the difference is too small to be ignored. Any one of the internal diameters calculated from the flight time echo delays can be used, or an average of the two internal diameters can be applied. Thus, the processing unit 213 can determine the real-time volumetric flow rate of the drug solution 101 in the intravenous catheter 102 by multiplying the linear flow rate and the cross-sectional area calculated from the internal diameter(s) ($d_e$) of the intravenous catheter 102, and convert the real-time volumetric flow rate into the flow rate electronic signal. The flow sensor module 200 illustrated in FIG. 5 is also suitable for the intravenous catheter 102 which is flexible and with an internal diameter of the cross-section is not fixed due to external forces. While the single-element transducers are capable of measuring Doppler signals when there are scattering particles in the drug solution 101, the face-to-face detecting elements mounted on the opposite side of the intravenous catheter 102 will offer a more accurate measurement of volumetric flow rate when the drug solution 101 is a clear solution. This design is workable both for the drug solution with scattering particles or not, since the ultrasound transducers 202 in the first face-to-face detecting element 200a and the second face-to-face detecting element 200b are all able to receive penetrated or reflected ultrasounds.

Figure 8:
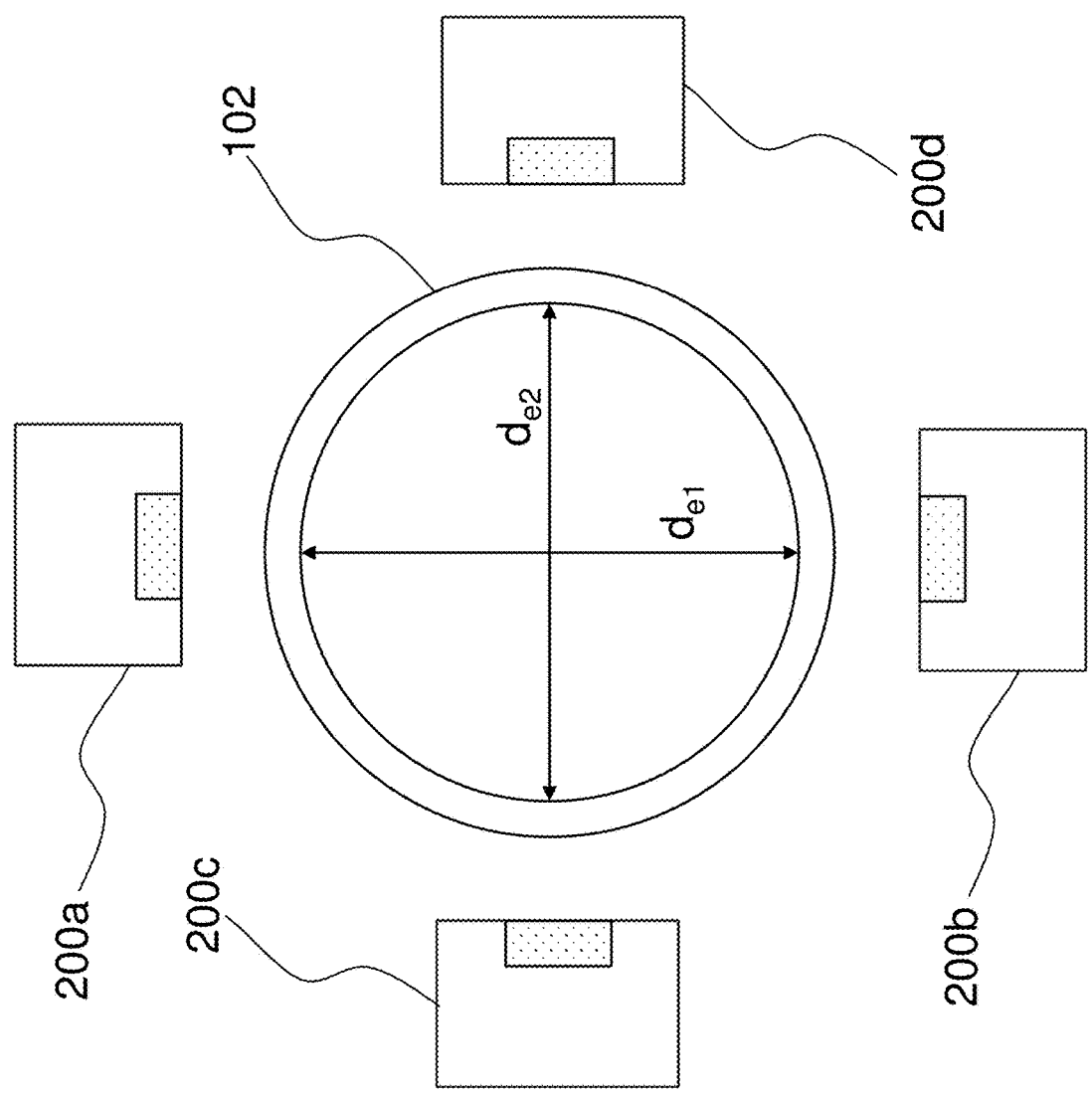
FIG. 8 shows two pairs of face-to-face detecting elements in the flow sensor module.

As mentioned above, there can be two or more pairs of face-to-face detecting elements used in the flow sensor module 200. Take two pairs of face-to-face detecting elements for example. Please see FIG. 8. The first face-to-face detecting element 200a and the second face-to-face detecting element 200b makes a first pair. A face-to-face detecting element 200c and a second face-to-face detecting element 200d makes a second pair. The first pair and the second pair should be perpendicular to each other. A first internal diameter $d_{e1}$ of the intravenous catheter 102 can be obtained from the first pair of face-to-face detecting elements. A second internal diameter $d_{e2}$ of the intravenous catheter 102 can be obtained from the second pair of face-to-face detecting elements. The first internal diameter $d_{e1}$ may be different from the second internal diameter $d_{e2}$. If there is a clear gap between the two internal diameters, the cross-sectional area of the intravenous catheter 102 may be obtained by $\pi(d_{e1})(d_{e2})$ (calculation formula of ellipse area). More than two pairs of face-to-face detecting elements may also be used. They can be located at different orientations across the cross-section of the intravenous catheter 102. For a flow sensor module 200 with 3 pairs of face-to-face detecting elements, two adjacent face-to-face detecting elements may be arranged with 60 degrees apart.

Figure 9:
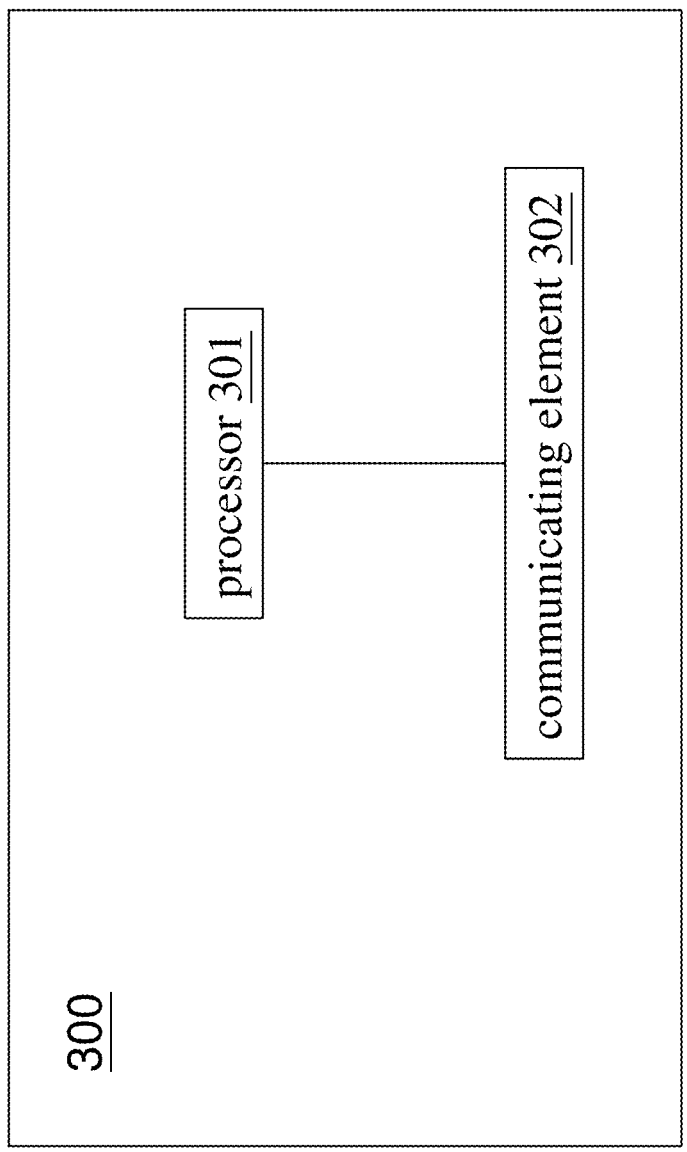
FIG. 9 is a block diagram of the communicating module.

The communicating module 300 is electrically and signally connected with the flow sensor module 200. The communicating module 300 can receive the flow rate electronic signal and deliver the flow rate electronic signal to an external agent 100 connected to it. In order to have a better understanding of the communicating module 300, please see FIG. 9. It is a block diagram of the communicating module 300. The communicating module 300 comprises a processor 301 and a communicating element 302. The processor 301 may be a single microchip and electrically and signally connected with the flow sensor module 200 to receive the flow rate electronic signal. In this embodiment, the connection is a wire. In other embodiment, the connection may be conductive tracks on a printed circuit board as a substrate for the flow sensor module 200 and the communicating module 300. The communicating element 302 is electrically connected to the processor 301. It is controlled by the processor 301 to wiredly or wirelessly deliver the flow rate electronic signal to the external agent connected to itself for analysis and display. Since the communicating element 302 can process wiredly or wirelessly connection, in practice, the communicating element 302 can a USB module, a Bluetooth module, or a Wi-Fi module. In this embodiment, the communicating element 302 is a Bluetooth module for wireless communication with the external agent. According to the spirit of the present invention, the external agent is used to display data in the flow rate electronic signal, analyze the data and process settings. Suitable type of devices of the external agent should be a smart phone, a tablet or a computer. A tablet 20 is used in the embodiment.

Preferably, an application (APP) can be installed in the tablet 20 (external agent). The APP is a software run to control the operation of the tablet 20 under a operating system. In this embodiment, the infusion module 100 is a set of a drip bag 110 and a roller clamp 120. Operator of the intravenous infusion system 10 need to adjust the infusion rate of the drug solution 101 in the intravenous catheter 102 in a desired degree by tuning the roller clamp 120 manually. If the real-time volumetric flow rate measured is different from a prescribed value, the operator (medical personnel) can use the roller clamp 120 to reduce or increase the infusion rate. By several rounds of back-and-forth adjustments using the roller clamp 120, the actual infusion rate can reach within an acceptable range to that prescribed by the physician. Thus, the APP can offer the service helps reducing workload.

The APP can be initiated to actuate an alert in sound, vibration, light signal, or visual images on a screen 21 of the tablet 20 when the real-time volumetric flow rate falls out of a safety window (a range that the flow rate of the drug solution 101 is acceptable). Meanwhile, the APP can be initiated to calculate and record the total volume of drug in the drug solution 101 infused from the onset of the process by integrating the real-time volumetric flow rate over the time elapsed (unit dose known). The APP also compares the real-time volumetric flow rate and the total volume of drug to an infusion rate and a dosage setting, respectively. The infusion rate is a target that the operator would like to run for the infusion. The dosage setting is a maximum medication setting and previously set by operating the APP. When the total volume of drug is close to the dosage setting, the APP will actuate an alert message from the tablet 20. If a slow-down of the real-time volumetric flow rate is obtained and lower than a preset value, the APP can actuate the tablet 20 to send an alert signal in sound, vibration, light signal, and/or images visual images on the screen 21 of the tablet 20 to alert the operator or medical personnel to take action to end an infusion process at the end of the infusion process. Preferably, the APP can be integrated with an infusion drug database, such that all settings of the tablet 20, an instantaneous infusion rate, and a real-time dosage are regularly checked with the infusion drug database to ensure safety of the patient during the infusion process.

For use of the drip bag 110 and the roller clamp 120, this measured real-time volumetric flow rate is used as a reference by the medical personnel to manually adjust the intravenous flow rate through the roller clamp 120 until it reaches the target value. Of course, the connection between the communicating module 300 and the tablet 20 can be wired. The communicating element 302 can further include a USB module and a USB cable can be applied for communicating. It is not limited by the present invention.

Figure 10:
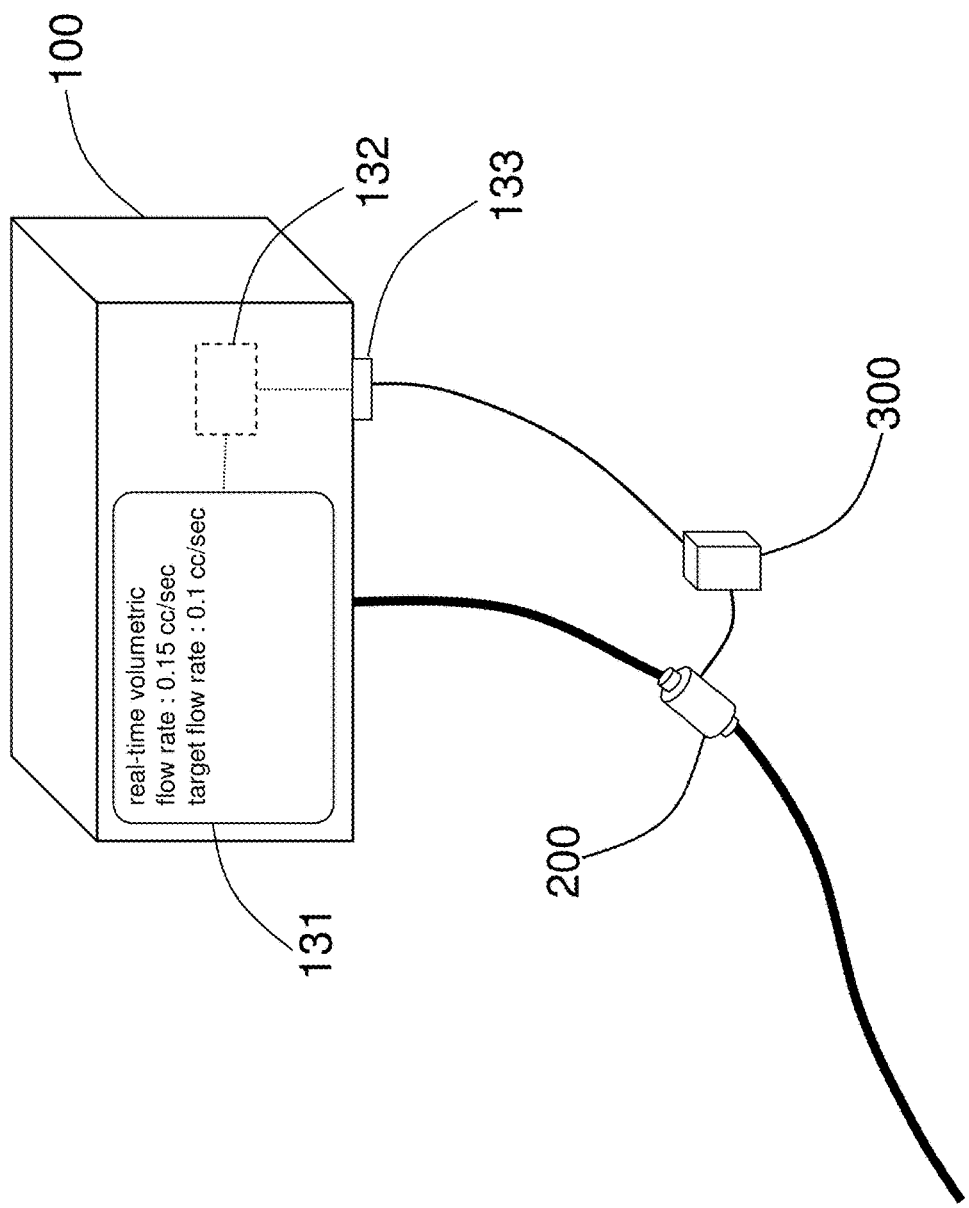
FIG. 10 shows another embodiment of an intravenous infusion system with real-time infusion rate monitoring and closed-loop infusion rate control according to the present invention.

Please refer to FIG. 10. FIG. 10 shows another embodiment of an intravenous infusion system 30 with real-time infusion rate monitoring and closed-loop infusion rate control according to the present invention. In order to reduce repeated description on the intravenous infusion system 30, some elements in the previous embodiments will be used in this embodiment. In FIG. 10, the same number of the symbol indicates the same element in the previous embodiment. The intravenous infusion system 30 comprises the infusion module 100, the flow sensor module 200 and the communicating module 300 as well. The differences between two embodiments are the infusion module 100 is an infusion pump and the communicating module 300 is wiredly connected to a micro-controller 133. The infusion module 100 has a screen 131 for display data and a control unit 132 for controlling the screen 131, electrically connected to the micro-controller 133 to fetch data (the flow rate electronic signal) from the communicating module 300 through a USB cable. In the intravenous infusion system 30, the external agent is the micro-controller 133 and electrically connected to the control unit 132 of the infusion pump. The micro-controller 133 compares the real-time volumetric flow rate to a pump target rate of the infusion pump in a clinical setting and adjusts a pump repetition rate of the infusion pump via the control unit 132 such that the flow rate of the drug solution 101 from the infusion pump approaches the pump target rate. If the real-time volumetric flow rate is higher than the clinical setting, the pump repetition rate of the infusion pump will be lowered by the micro-controller 133. If the real-time volumetric flow rate is lower than the clinical setting, the pump repetition rate of the infusion pump will be increased by the micro-controller 133. With this design, a mechanically less precise infusion pump can deliver the same infusion accuracy similar to that offered by a high-end infusion pump. Therefore, an infusion rate of the drug solution 101 in the intravenous catheter 102 can be adjusted to close to and be stable at the pump target rate after several loops of back-and-forth adjustments.

Figure 11:
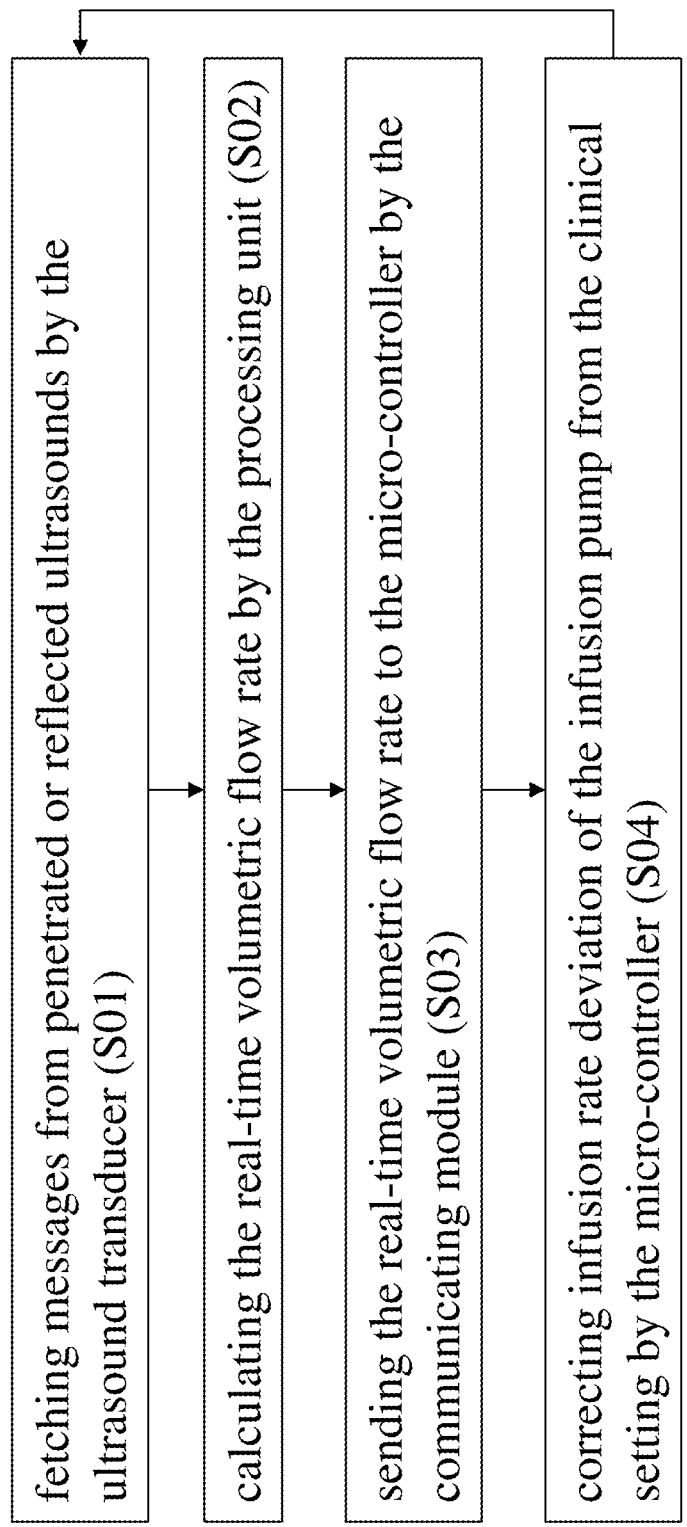
FIG. 11 is a flow chart of operating the closed-loop infusion rate control.

In this case, the intravenous infusion system 30 forms a closed-loop control on infusion and the micro-controller 133 of the infusion pump can correct infusion rate deviation from the clinical setting and/or stops an infusion process according to the clinical setting. The closed-loop control can be illustrated by a flow chart in FIG. 11. There are several steps. A first step is fetching messages from penetrated or reflected ultrasounds by the ultrasound transducer (S01). Then, a second step is calculating the real-time volumetric flow rate by the processing unit 203 (S02). A third step is sending the real-time volumetric flow rate to the micro-controller 133 by the communicating module 300 (S03). Last, a fourth step is correcting infusion rate deviation of the infusion pump from the clinical setting by the micro-controller 133 (S04). After S04, the infusion pump adjusts its pump repetition rate and the closed-loop control is formed. The intravenous infusion system 30 process the closed-loop control so that the infusion rate of the drug solution 101 in the intravenous catheter 102 can be adjusted to close to the pump target rate by repeating S01 to S04 again and again. The new infusion pump architecture does self-calibration based on the real-time volumetric flow rate measured by the flow sensor module 200 and is potentially less expensive because it does not require such precise mechanical parts and assembly as current on-market infusion pumps. For example, a less-accurate infusion pump with active feedback can offer the same accuracy in infusion rate control as an open-loop high-precision electro-mechanical pump for a fraction of the manufacturing cost.

There are two advantages associated with this new closed-loop infusion pump architecture. First, through an infusion rate feedback loop, the infusion pump calibrates itself every time it operates, removing the need for manual calibration and saving on personnel costs. Second, the feedback mechanism makes it possible that a mechanically less precise infusion pump can deliver the same infusion rate accuracy as a high-end infusion pump. This offers an advantage in manufacture cost for the intravenous infusion system.

One or more intravenous infusion systems equipped with aforementioned flow sensor modules 200 can be arranged to report to as well as being monitored and managed by one smart (portable) device including the tablet 20 or a smart phone. As a result, by using this smart device, one or a small number of medical personnel can manage and monitor one or more patients during their infusion procedures. Multiple patient's infusion process and progress is displayed on the smart device in real-time. The medical personnel will be alerted by the smart device of any infusion process abnormality or if any patient's procedure is close to an end of the infusion process.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims, which are to be accorded with the broadest interpretation so as to encompass all such modifications and similar structures.

What is claimed is:

1. An intravenous infusion system, comprising:
   an infusion module, providing drug solution through an intravenous catheter;
   a flow sensor module, installed around an outer periphery of the intravenous catheter, transmitting ultrasounds to the intravenous catheter and receiving ultrasounds reflected or penetrated therefrom to determine a real-time volumetric flow rate of the drug solution in the intravenous catheter, and converting the real-time volumetric flow rate into a flow rate electronic signal; and
   a communicating module, electrically and signally connected with the flow sensor module, receiving the flow rate electronic signal and delivering the flow rate electronic signal to an external agent connected thereto.

2. The intravenous infusion system according to claim 1, wherein the infusion module is an infusion pump, or a set of a drip bag and a roller clamp.

3. The intravenous infusion system according to claim 1, wherein the flow sensor module comprises at least one flow sensor attached to the outer periphery of the intravenous catheter when an internal diameter of the intravenous catheter is substantially fixed.

4. The intravenous infusion system according to claim 3, wherein the flow sensor is a hot-wire flow sensor, a differential-pressure-pair flow sensor, an electromagnetic flow sensor, or an ultrasonic flow sensor.

5. The intravenous infusion system according to claim 1, wherein the communicating module comprises:
   a processor, electrically and signally connected with the flow sensor module to receive the flow rate electronic signal; and
   a communicating element, electrically connected to and controlled by the processor to wiredly or wirelessly deliver the flow rate electronic signal to the external agent connected thereto for analysis and display.

6. The intravenous infusion system according to claim 5, wherein the communicating element is a USB module, a Bluetooth module, or a Wi-Fi module.

7. The intravenous infusion system according to claim 1, wherein the flow sensor module comprises:
   at least one ultrasound transducer, transmitting ultrasounds with a center frequency equal to or higher than 100 k Hz, receiving reflected ultrasounds from the intravenous catheter and transforming the reflected ultrasounds into a sensing electronic signal; and
   a processing unit, electrically connected to the at least one ultrasound transducer, comparing one transmitted ultrasound with a corresponding reflected ultrasound using the sensing electronic signal to find Doppler ultrasound frequency shift generated therefrom, calculating a linear flow rate of the drug solution with the Doppler ultrasound frequency shift, finding a flight time echo delay between two reflected ultrasounds generated from the same transmitted ultrasound from two opposite inner surfaces of the intravenous catheter, respectively, to calculate the internal diameter of the intravenous catheter, determining the real-time volumetric flow rate of the drug solution in the intravenous catheter by multiplying the linear flow rate and a cross-sectional area calculated from the internal diameter of the intravenous catheter, and converting the real-time volumetric flow rate into the flow rate electronic signal.

8. The intravenous infusion system according to claim 7, wherein the ultrasound transducer is a piezoelectric transducer, a capacitive micromachined ultrasound transducer, or a piezoelectric micromachined ultrasound transducer.

9. The intravenous infusion system according to claim 1, wherein the flow sensor module comprises:
   at least one pair of face-to-face detecting elements fitted around the intravenous catheter, wherein the face-to-face detecting element comprises at least one ultrasound transducer, transmitting ultrasounds with a center frequency equal to or higher than 100 k Hz, receiving reflected or penetrated ultrasounds from the intravenous catheter and transforming the reflected or penetrated ultrasounds into a sensing electronic signal; and
   a processing unit, electrically connected to the at least one pair of face-to-face detecting elements, comparing one transmitted ultrasound with a corresponding penetrated ultrasound using the sensing electronic signal to find Doppler ultrasound frequency shift generated therefrom, calculating a linear flow rate of the drug solution with the Doppler ultrasound frequency shift, finding a flight time echo delay between two reflected ultrasounds generated from the same transmitted ultrasound from two opposite inner surfaces of the intravenous catheter, respectively, to calculate the internal diameter of the intravenous catheter, determining the real-time volumetric flow rate of the drug solution in the intravenous catheter by multiplying the linear flow rate and a cross-sectional area calculated from the internal diameter(s) of the intravenous catheter, and converting the real-time volumetric flow rate into the flow rate electronic signal.

10. The intravenous infusion system according to claim 9, wherein the ultrasound transducer is a piezoelectric transducer, a capacitive micromachined ultrasound transducer, or a piezoelectric micromachined ultrasound transducer.

11. The intravenous infusion system according to claim 2, wherein the external agent is a micro-controller and electrically connected to a control unit of the infusion pump, comparing the real-time volumetric flow rate to a pump target rate of the infusion pump in a clinical setting and adjusts a pump repetition rate of the infusion pump via the control unit such that the flow rate of the drug solution from the infusion pump approaches the pump target rate.

12. The intravenous infusion system according to claim 1, wherein the external agent is a smart phone, a tablet or a computer.

13. The intravenous infusion system according to claim 12, wherein an application (APP) is installed in the external agent.

14. The intravenous infusion system according to claim 13, wherein the APP is initiated to calculate and record the total volume of drug solution infused from the onset of the process by integrating the real-time volumetric flow rate over the time elapsed, compare the real-time volumetric flow rate and the total volume of drug to an infusion rate and a dosage setting, respectively, and actuate an alert message from the external agent when the total volume of drug is close to the dosage setting.

15. The intravenous infusion system according to claim 13, wherein the APP is initiated to actuate an alert in sound, vibration, light signal, or visual images on a screen of the external agent when the real-time volumetric flow rate falls out of a safety window when the infusion module is a set of a drip bag and a roller clamp.

16. The intravenous infusion system according to claim 13, wherein the APP is integrated with an infusion drug database such that all settings of the external agent, an instantaneous infusion rate, and a real-time dosage are regularly checked with the infusion drug database to ensure safety of the patient during an infusion process.

17. The intravenous infusion system according to claim 13, wherein when the infusion module is a set of a drip bag and a roller clamp, if a slow-down of the real-time volumetric flow rate is obtained and lower than a preset value, the APP actuates the external agent to send an alert signal in sound, vibration, light signal, and/or images visual images on a screen of the external agent to alert the medical personnel to take action to end an infusion process at the end of the infusion process.

18. The intravenous infusion system according to claim 2, wherein when the infusion module is an infusion pump, the intravenous infusion system forms a closed-loop control on infusion with a micro-controller and electrically connected to a control unit of the infusion pump corrects infusion rate deviation from a clinical setting and/or stops an infusion process according to the clinical setting.

19. The intravenous infusion system according to claim 18, if the real-time volumetric flow rate is higher than the clinical setting, the pump repetition rate of the infusion pump will be lowered by the micro-controller; if the real-time volumetric flow rate is lower than the clinical setting, the pump repetition rate of the infusion pump will be increased by the micro-controller.

* * * * *